(12) United States Patent
Van Immerseel et al.

(10) Patent No.: US 8,697,052 B2
(45) Date of Patent: Apr. 15, 2014

(54) METHOD FOR ALLEVIATING INTESTINAL PROBLEMS AND NOVEL BACTERIAL STRAINS THEREFOR

(75) Inventors: Filip Van Immerseel, Eke (BE); Frank Pasmans, St Pieters Kapelle (BE); Richard Ducatelle, Wortegem-Petegem (BE); Benedikt Sas, Stekene (BE); Venessa Eeckhaut, Vlierzele (BE); Freddy Haesebrouck, Knokke-Heist (BE)

(73) Assignee: Universiteit Gent, Ghent (BE)

( * ) Notice: Subject to any disclaimer, the term of this patent is extended or adjusted under 35 U.S.C. 154(b) by 177 days.

(21) Appl. No.: 13/138,461

(22) PCT Filed: Feb. 22, 2010

(86) PCT No.: PCT/EP2010/052184
§ 371 (c)(1),
(2), (4) Date: Oct. 11, 2011

(87) PCT Pub. No.: WO2010/094789
PCT Pub. Date: Aug. 26, 2010

(65) Prior Publication Data
US 2012/0027734 A1 Feb. 2, 2012

(30) Foreign Application Priority Data
Feb. 23, 2009 (GB) .................................. 0903016.4

(51) Int. Cl.
*A01N 63/00* (2006.01)
*C12N 1/20* (2006.01)

(52) U.S. Cl.
USPC ..................................... 424/93.4; 435/252.1

(58) Field of Classification Search
None
See application file for complete search history.

(56) References Cited

U.S. PATENT DOCUMENTS

2007/0258953 A1   11/2007   Duncan et al.

FOREIGN PATENT DOCUMENTS

WO   WO 2004/085628   10/2004
WO   WO 2008/091170   7/2008
WO   WO 2010/094789   8/2010

OTHER PUBLICATIONS

Van Immerseel et al., Butyric acid-producing anaerobic bacteria as a novel probiotic treatment approach for inflammatory bowel disease, Journal of Medical Microbiology, Feb. 2010, pp. 141-143, vol. 59, No. 2.
Eeckhaut et al., The anaerobic Butyrate-Producing Strain *Butyricicoccus pullicaecorum* Decreases Colonic Inflammation and Ulceration in a TNBS-Induced Colitis Rat Model, 5$^{th}$ Probiotics and Prebiotics and New Foods Meeting, Sep. 13-15, 2009.
Eeckhaut et al., *Butyricicoccus pullicaecorum* gen. nov., sp. nov., an anaerobic, butyrate-producing bacterium isolated from the caecal content of a broiler chicken, International Journal of Systematic and Evolutionary Microbiology, 2008, pp. 2799-802, vol. 58.
Sokol et al., *Faecalibacterium prausnitzii* is an anti-inflammatory commensal bacterium identified by gut microbiota analysis of Crohn disease patients, Proceedings of the National Academy of Sciences of the United States of America, Oct. 28, 2008, pp. 16731-16736, vol. 105, No. 43.
Morrison et al., Butyrate production from oligofructose fermentation by the human faecal flora: what is the contribution of extracellular acetate and lactate?, Sep. 2006, pp. 570-577, vol. 96, No. 3.
PCT International Search Report, PCT/EP2010/052184, dated May 25, 2010.
DSMZ database search printout, Name: *Butyricicoccus pullicaecorum*, DSM No. 23266, Type strain, printed Nov. 8, 2013.
Peterson et al., Metagenomic Approaches for Defining the Pathogenesis of Inflammatory Bowel Diseases, Cell Host Microbe, Jun. 12, 2008, pp. 417-427—vol. 3, No. 6.

*Primary Examiner* — Vera Afremova
(74) *Attorney, Agent, or Firm* — TraskBritt

(57) ABSTRACT

The present invention relates to butyrate producing bacterial strains related to the species *Butyricoccus pullicaecorum* to be used in the prevention and/or treatment of intestinal health problems. The present invention therefore provides methods and compositions that overcome the problems associated with the currently used methods for administering butyric acid in the treatment of intestinal health problems in humans and/or animals.

7 Claims, No Drawings

METHOD FOR ALLEVIATING INTESTINAL PROBLEMS AND NOVEL BACTERIAL STRAINS THEREFOR

CROSS-REFERENCE TO RELATED APPLICATIONS

This is a national phase entry under 35 U.S.C. §371 of international Patent Application PCT/EP2010/052184, filed Feb. 22, 2010, published in English as International Patent Publication WO 2010/094789 A1 on Aug. 26, 2010, which claims the benefit under Article 8 of the Patent Cooperation Treaty to United Kingdom Patent Application Serial No. 0903016.4, filed Feb. 23, 2009.

FIELD OF THE INVENTION

The present invention relates to butyrate producing bacterial strains related to the species *Butyricoccus pullicaecorum* to be used in the prevention and/or treatment of intestinal health problems. The present invention therefore provides methods and compositions that overcome the problems associated with the currently used methods for administering butyric acid in the treatment of intestinal health problems in humans and/or animals.

BACKGROUND OF THE INVENTION

Inflammatory bowel disease (IBD) refers to two chronic diseases that cause inflammation of the intestines: ulcerative colitis and Crohn's disease. Whereas ulcerative colitis is an inflammatory disease of the large intestine that affects the mucosa of the intestine which becomes inflamed and develops ulcers, Crohn's disease most commonly affects the last part of the small intestine, the terminal ileum, and parts of the large intestine. However, Crohn's disease is not limited to these areas and can occur in any part of the digestive tract. Crohn's disease causes inflammation that extends much deeper into the layers of the intestinal wall than ulcerative colitis does. Crohn's disease generally tends to involve the entire bowel wall, whereas ulcerative colitis affects only the lining of the bowel.

Medical research has not determined yet what causes inflammatory bowel disease. It is however believed that a number of factors may be involved, such as the environment, diet, and possibly genetics. The drug treatment for IBD usually consists of anti-inflammatory drugs and immunosuppressive agents. However, current therapy to control IBD is not always effective, and surgical procedures are still necessary in many cases. Today, about 70 to 80% of patients with Crohn's disease and 30 to 40% with ulcerative colitis ultimately require surgery, indicating the lack of efficiency of the currently used therapeutics.

With respect to intestinal health problems in animals such as dysbacteriosis, currently antibiotics are used as a treatment. Also a wide variety of feed additives are on the market, including essential oils, fatty acid preparations, pre- and probiotics, and combinations of products of which it is claimed that they improve gastrointestinal tract health. Their use however is empirical and their efficacy is not scientifically proven.

Currently butyric acid is used in the treatment of IBD, but the actual delivery of butyric acid into the gastrointestinal tract is problematic. Several mechanisms have already been proposed, including the use of butyrate coated tablets, butyrate enemas or the use of natural fermentation in the gastrointestinal tract using dietary fibre. These currently known approaches show significant drawbacks. When using butyric coated tablets the problem lays in the release of their content at the intended location and because of the inter-individual differences in gastrointestinal tract lumen pH and transit time (Ibekwe et al., 2006; Roda et al. 2007) the release cannot be optimised. Moreover taste of the tablets is very unpleasant. The use of rectal butyric acid enemas on the other hand is hampered by a low compliance rate and a short and discontinuous exposure of the colon mucosa to butyrate (Breuer et al., 1997). When using the fermentation of dietary fibre for butyrate production the use of resistant starch and oligofructose have been associated with a greater butyrate production (Morrison et al 2006). The stimulation of butyrate production however depends on the presence of bacteria expressing butyryl CoA:acetyl CoA transferase and the regional differences in lactate utilising, butyrate producing bacteria (Morrison et al 2006). Therefore, this approach is not uniform and the outcome cannot be predicted. For the treatment of dysbacteriosis in animals at this moment a powder form or coated butyric acid administration to the feed is used. This results however in similar problems as stated above, additionally having a negative sensory aspect that is unfavourable for the animals.

Another approach to deliver butyric acid into the gastrointestinal tract is the administration of butyric acid-producing bacteria, enabling in situ production of butyric acid. In this regard, Sokol et al. (Proc Natl Acad Sci USA, 2008: 16731) disclose that the butyrate-producing bacterium *Faecalibacterium prausnitzii* or culture supernatants of this bacterium are capable in decreasing inflammation and necrosis in rodent IBD models. WO 2004/085628 further discloses that lactic acid-utilizing bacteria which also produce butyric acid, such as the bacterium species *Anaerostipes caccae*, might be used in a method for treating diseases associated with a high dosage of lactic acid such as IBD.

Eeckhaut et al. 2008 recently described the isolation of butyrate-producing bacterial isolates belonging to the novel species *Butyricicoccus pullicaecorum*. The latter novel species has as type strain the isolate $25\text{-}3^T$ which is deposited at the public BCCM/LMG bacterial collection as *B. pullicaecorum* LMG24109.

The present invention relates to the unexpected finding that butyrate producing strains related to the species *B. pullicaecorum* are superior in their capability to prevent or cure intestinal health problems of humans or animals compared to other butyrate-producing species such as *Faecalibacterium prausnitzii*, *Anaerostipes caccae* or *Anaerostipes butyricus*. Hence the present invention relates to the delivery of *B. pullicaecorum* which is much more effective than comparable delivery methods and further also overcomes all the disadvantages as stated above.

The present invention thus solves the problem of finding more efficient and effective compounds and methods to treat intestinal health problems in humans or animals. The present invention provides new compositions for prophylaxis and/or treatment of intestinal health problems in humans or animals.

SUMMARY OF THE INVENTION

The present invention provides a novel and inventive method that overcomes the problems associated with the currently used methods for administering butyric acid in the treatment of intestinal health problems in humans and/or animals.

It has been found that certain butyrate producing strains according to the present invention can be used as a medicament and, more specifically, in the prevention and/or treatment of intestinal health problems occurring in humans and/ or animals. The butyrate producing strains of the present invention, when administered to humans and/or animals, are able to colonize the gastrointestinal tract. This colonization provides that the butyrate producing strains of the present invention enable the in situ production of butyric acid in the gastrointestinal tract and more specifically the colonization of and the in situ production of butyric acid in the colon.

The term 'intestinal health problem' refers to any intestinal disease in humans and/or animals and/but specifically relates to intestinal bowel disease in humans and dysbacteriosis in animals.

The butyrate producing strains for use according to the present invention specifically relate to an isolated strain referred to as *Butyricicoccus pullicaecorum*, deposited at the public BCCM/LMG bacterial collection as *B. pullicaecorum* LMG 24109.

According to the invention, the butyric acid producing strains for use in the prophylaxis and/or treatment of intestinal health problems of humans and/or animals, are strains from the *Clostridium* cluster IV.

In a preferred embodiment, the present invention relates to butyric acid producing strains for use in the prophylaxis and/or treatment of intestinal health problems of humans and/or animals, characterized therein that said butyric acid producing strains are chosen from the group comprising *Butyricicoccus pullicaecorum*, deposited at the public BCCM/LMG bacterial collection as *B. pullicaecorum* LMG 24109 and strains having a 16S rRNA showing at least 93% (i.e. 93%, 94%, 95%, 96%, 97%, 98%, 99% A or 100%) homology to the 16S rRNA sequence of *Butyricicoccus pullicaecorum* characterized by SEQ ID No 1.

The present invention also relates to a probiotic composition, wherein the composition comprises a therapeutical effective amount of the isolated bacterial strain as defined above and/or a culture supernatant thereof having a therapeutic effect and/or a metabolite thereof having a therapeutic effect.

These and further aspects and embodiments are described in the following sections and in the claims.

DETAILED DESCRIPTION OF THE INVENTION

The present invention relates according to a first aspect to certain butyrate producing bacterial strains for use as a medicament, and more specifically, for use in the prevention and treatment of intestinal health disorders in human and/or animals.

Indeed, the present invention discloses that butyrate producing strains related to the species *B. pullicaecorum* are superior in their capability to prevent or cure intestinal health problems of humans or animals compared to other butyrate-producing species such as *Faecalibacterium prausnitzii*, *Anaerostipes caccae* or *Anaerostipes butyricus*. For example, the present invention demonstrates that colon weight, colon index and the degree of ulceration—which all reflect the severity of disease inflammation—, and/or other well-known parameters of disease severity, are significantly reduced when treated with *B. pullicaecorum* compared to a positive control or compared to the treatments with the other 3 bacterial species.

Another aspect of the present invention relates to butyrate producing strains related to the species *B. pullicaecorum* which are at least comparable, and preferably superior to *Faecalibacterium prausnitzii* in their capability to prevent or cure intestinal health problems in humans or animals.

The term a 'medicament', also referred to as pharmaceutical drug, medicine or medication, can be defined as any chemical substance or composition of chemical substances intended for use in the medical diagnosis, cure, treatment, or prevention of disease. Said medicament comprises at least one biologically active ingredient and possibly at least one excipient or carrier which is the substance of the tablet or dosage form of the medicament, or the liquid the active ingredient is suspended in, and possibly other materials that are pharmaceutically inert. Suitable carriers, excipients or other materials are known to the skilled man. The 'medicament' may be administered by any suitable method within the knowledge of the skilled man. The preferred route of administration is oral administration. However, the dosage and mode of administration will depend on the individual/animal.

As used herein, the terms "butyrate" ("butyrate" being a salt or ester of "butyric acid") and "butyric acid" are used as synonyms and refer to a carboxylic acid ($CH_3$—$CH_2$—$CH_2$—COOH) with structural formula (I).

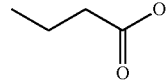

Formula (I)

More preferably the butyrate producing bacterial strains of the invention refer to bacterial strains that produce butyrate as the major metabolite.

More preferably the butyrate producing bacterial strains for use according to the present invention are *Butyricicoccus pullicaecorum* and/or strains showing at least 93% (i.e. 94%, 95%, 96%, 97%, 98%, 99% or 100%) homology to the 16S rRNA sequence of *B. pullicaecorum* characterized by SEQ ID No 1. More preferably, the bacterial strains according to the present invention show at least 94%, 95%, 96%, 97%, 98%, 99%/0 or 100% homology to the 16S rRNA sequence of *B. pullicaecorum* characterized by SEQ ID No 1. Even more preferably, the bacterial strains according to the present invention show at least 95%, 96%, or 98% homology to the 16S rRNA sequence of *B. pullicaecorum* characterized by SEQ ID No 1. Preferably the butyrate producing bacterial strains are capable of producing butyric acid under substantially anaerobic conditions.

The butyrate producing bacterial strain *Butyricicoccus pullicaecorum* belongs to the phylogenetic group of *Clostridium leptum* (=*Clostridium* Cluster IV).

The *Clostridium* cluster IV contains isolates of a mixture of genera, including *Clostridium*, *Eubacterium* and *Ruminococcus*. A number of species are mesophilic and cellulolytic, including *Ruminococcus albus*, *Ruminococcus flavefaciens* and *C. cellulosi*. Non-cellulolytic strains are also present, although many of these will degrade other polysaccharides. The members of cluster IV are phenotypically heterogeneous and exhibit a broad chromosomal DNA G+C content range.

In a preferred embodiment butyrate producing strain provided by the present invention refers to a *Butyricicoccus pullicaecorum* strain which has been deposited at the public BCCM/LMG bacterial collection as *B. pullicaecorum* LMG24109 on Apr. 26, 2007. This deposited *Butyricicoccus pullicaecorum* strain is characterized by a 16S rRNA sequence having SEQ ID No 1. The butyric acid producing strain *Butyricicoccus pullicaecorum* has also been deposited at the Culture Collection, University of Göteborg (CCUG) as *B. pullicaecorum* CCUG 55265. Different isolates of *B. pullicaecorum* and the type strain 25-3$^T$ have been well-characterized by Eeckhaut et al. 2008 (International Journal of Systematic and Evolutionary Microbiology: 2799) which is hereby enclosed by reference.

The 16S rRNA sequences of *B. pullicaecorum* (SEQ ID No 1) is provided in Table 1.

The GC-content of *B. pullicaecorum* is about 54%. Furthermore *B. pullicaecorum* cells have a coccoid form. The biochemical characteristics of *B. pullicaecorum* are provided in Table 2.

It has been found that the butyrate producing strains according to the present invention can be used in the prevention and/or treatment of intestinal health problems occurring in humans and/or animals. The novel butyrate producing strains of the present invention, when administered to humans and/or animals, are able to colonize the gastrointestinal tract. This colonization provides that the butyrate producing strains of the present invention enable the in situ production of butyric acid in the gastrointestinal tract and more specifically the colonization of and the in situ production of butyric acid in the colon. By providing these butyrate producing strains the disadvantages known in the prior art are overcome.

This type of delivery process is compared to the known methods much easier, the butyric acid is released at the intended location during a prolonged and continued period of time. Additionally, the process of the present invention is not dependent on the presence of specific micro-organisms in the gastrointestinal tract. Furthermore, the inventors have found that a significant butyrate production is yielded in situ by the colonizing butyric acid producing bacteria of the present invention.

The present invention therefore provides a method that overcomes the problems associated with the currently used methods for administering butyric acid in the treatment of intestinal health problems in humans and/or animals.

TABLE 1

*Butyricicoccus pullicaecorum* 16S rRNA sequence
(SEQ ID No 1)

tagtttgatcctggctcaggatgaacgctggcggcgtgcctaacacat gcaagtcgaacggagttgtttgaggaaatccttcgggatggaatcttc caacttagtggcggacgggtgagtaacgcgtgagcaatctgcctttca gaggggataacagccggaaacggctgctaataccgcataatgcattg aattcgcatgttttgatgccaaagattttatcgctgaaagatgagct cgcgtctgattagctagttggcggggtaacggcccaccaaggcgacga tcagtagccggactgagaggttgaacggccacattgggactgaggaca cggcccagactcctaccgggaggcagcagtgggaatattgcgcaatg ggggcaaccctgacgcagcaacgccgcgtgattgatgaaggtcttcgg attgtaaaaatctttaatcagggacgaaacaaatgacggtacctgaag aataagctccggctaactacgtgccagcagccgcggtaatacgtaggg agcaagcgttatccggatttactgggtgtaaagggcgtgtaggcgggc ttgtaagttggaagtgaaatctcggggcttaaccccgaaactgctttc aaaactgcgagtcttgagtgatggagaggcaggcggaattcccagtgt agcggtgaaatgcgtagatattgggaggaacaccagtggcgaaggcgg cctgctggacattaactgacgctgaggcgcgaaagcgtggggagcaaa caggattagataccctggtagtccacgccgtaaacgatggatactagg TABLE 1 -continued

*Butyricicoccus pullicaecorum* 16S rRNA sequence
(SEQ ID No 1)

tgtgggaggtattgacccttccgtgccggagttaacacaataagtat cccacctggggagtacggccgcaaggttgaaactcaaaggaattgacg ggggcccgcacaagcagtggagtatgtggtttaattcgaagcaacgcg caagaaccttaccaagtcttgacatcccgatgaccgctcyagagatag ggcttttcttcggaacatcggtgacaggtggtgcatggttgtcgtcag ctcgtgtcgtgagatgttgggttaagtcccgcaacgagcgcaacccctt acgggttagttgctacgcaagagcactctagccggactgccgttgaca aaacggaggaaggtggggacgacgtcaaatcatcatgcccttatgac ttgggctacacacgtactacaatggcagtcatacagagggaagcaaaa ccgcgaggtggagcaaatccctaaaagctgtcccagttcagattgcag gctgcaactcgcctgcatgaagtcggaattgctagtaatcgcggatca gcatgccgcggtgaatacgttcccgggccttgtacacaccgcccgtca caccatgagagccggtaatacccgaagtccgtagtctaaccgcaagga ggacgcggccgaaggtaggactggtaattgggacgaagtcgt

TABLE 2

| Biochemical characteristics | |
|---|---|
| | *B. pullicaecorum* |
| ureum | − |
| glucose | + |
| mannitol | − |
| lactose | − |
| saccharose | + |
| maltose | + |
| salicine | + |
| xylose | + |
| arabinose | − |
| gelatine | − |
| esculine | + |
| glycerol | − |
| cellobiose | + |
| mannose | + |
| melezitose | − |
| sorbitol | − |
| raffinose | − |
| rhamnose | − |
| trehalose | + |

As indicated above, the butyrate producing strains for use according to the present invention also refer to *Butyricicoccus pullicaecorum* related strains' having more than 93%, 94%, 95%, 96%, 97%, 98%, 99% or 100% homology with the 16S rRNA sequence as depicted in SEQ ID No 1. Preferably the strains having 16S rRNA sequences with more than 93%, 94%, 95%, 96%, 97%, 98%, 99% or 100% homology with the 16S rRNA sequence of *Butyricicoccus pullicaecorum* are isolated from humans.

In this application the term "substantially anaerobic" has its ordinary meaning and refers to conditions in which there is little or no free oxygen available. With respect to a natural environment it refers to one where there is little or no free oxygen. As a way of an example, the conditions in the gastrointestinal tract of animals and/or humans can be considered as being substantially anaerobic. Some artificial fermentation processes are also known to be carried out in an anaerobic environment.

The present invention further relates to the use of butyric acid producing strains for the manufacturing of a preparation for the prophylaxis and/or treatment of intestinal health problems, characterized therein that said butyric acid producing strains are chosen from *Butyricicoccus pullicaecorum* deposited at the public BCCM/LMG bacterial collection as *B. pullicaecorum* LMG24109 and strains showing at least 93%, 94%, 95%, 96%, 97%, 98%, 99% or 100% homology to the 16S rRNA sequence of *Butyricicoccus pullicaecorum* characterized by SEQ ID No 1.

The present invention also relates to the use of butyric acid producing strains for the prophylaxis and/or treatment of intestinal health problems, characterized therein that said butyric acid producing strains are chosen from *Butyricicoccus pullicaecorum* deposited at the public BCCM/LMG bacterial collection as *B. pullicaecorum* LMG24109 and strains showing at least 93%, 94%, 95%, 96%, 97%, 98%, 99% A or 100% homology to the 16S rRNA sequence of *Butyricicoccus pullicaecorum* characterized by SEQ ID No 1. An example to determine the latter 'homology' is for example described by Eeckhaut et al. 2008 (International Journal of Systematic and Evolutionary Microbiology: 2799)

As used herein, the term "16S rRNA" refers to a nucleic acid sequence of about 1542 nucleotides which is a component of the small prokaryotic ribosomal subunit (30S). The 16S rRNA is known to act as a scaffold defining the positions of the ribosomal proteins. The 16S rRNA sequence is commonly used for phylogenetic studies, as it is known to be a highly conserved sequence. Comparative analysis of 16S rRNA sequences from thousands of organisms has demonstrated the presence of oligonucleotide signature sequences.

As used herein, the term "homology" refers to the sequence similarity of the nucleic acids. For example, in general, if two nucleic acids have identical sequences they show a 100% homology. A change in the nucleotide sequence of one of the nucleic acids reduces the percentage of homology. In general, the percentage homology quantifies the degree of identity between two nucleic acid sequences.

In yet another embodiment, the present invention provides that the intestinal health problems occur in humans and/or animals wherein the intestinal health problems are inflammatory bowel diseases such as preferably inflammatory bowel diseases such as ulcerative colitis or Crohn's disease. In another embodiment, the intestinal health problems are associated with the colonization by pathogenic microorganism of the gastrointestinal tract of humans and/or animals. Preferably the intestinal health problems are caused by *Clostridium perfringens* or *Clostridium difficile*.

In yet another embodiment, the present invention provides that the intestinal health problem in animals is dysbacteriosis.

Dysbacteriosis refers to a non-specific bacterial enteritis which causes an inflammation of the small intestine and/or a disruption in the normal flora of the gastrointestinal tract. This condition is especially seen in, preferably rapidly growing, broiler chickens with good food intake. Up till now however, no single bacterium was found to be responsible.

In another embodiment, the present invention provides that the butyric acid producing strains for use according to the present invention are present in a composition comprising an effective amount of said butyric acid producing strains. The term 'effective amount' refers to an amount of bacteria which is sufficiently large to be effectively used to prevent, treat or alleviate intestinal health problems in humans or animals.

The present invention relates in a preferred embodiment to a composition and preferably a probiotic composition, wherein the composition comprises a therapeutical effective amount of the isolated strains as defined above according to the present invention and/or a culture supernatant thereof and/or a metabolite thereof. Said 'culture supernatant thereof' refers to the metabolites which are secreted by the bacteria and which can be used as a medicament as is claimed for the bacteria themselves. In other words, said culture supernatant can be used as a medicament, preferably in order to prevent, treat or alleviate intestinal health problems, such as IBD or dysbacteriosis, of humans or animals. The term 'metabolite thereof' refers to any intermediate or final product of bacterial metabolism (i.e. both primary and secondary metabolites such proteins, peptides, fatty acids, pigments, antibiotics and the like . . . ) and is thus not restricted to the secreted metabolites as is the case for the term 'culture supernatant' as indicated above. All the metabolites of the present invention are metabolites which are capable to be used as a medicament, preferably in order to prevent, treat or alleviate intestinal health problems, such as IBD or dysbacteriosis, of humans or animals.

As used herein, the term "probiotic composition" refers to a composition comprising probiotics. Probiotics are dietary supplements and live microorganisms containing beneficial bacteria or yeasts. More specifically, probiotics refer to live microorganisms which when administered in adequate amounts confer a health benefit on the host. Lactic acid bacteria are the most common type of microorganisms used. Strains of the genera *Lactobacillus* and *Bifidobacterium*, are the most widely used probiotic bacteria. The probiotic bacterial cultures assist the body's naturally occurring gastrointestinal tract flora, to re-establish themselves.

In a preferred embodiment of the present invention, *B. pullicaecorum* according to the present invention and/or strains showing at least 93%, 94%, 95%, 96%, 97%, 98%, 99% or 100% homology to the 16S rRNA sequence of *B. pullicaecorum* characterized by SEQ ID No 1 are preferably used in a probiotic composition.

In yet another embodiment the probiotic composition of the present invention comprises butyric acid producing strains to be used according to the invention as defined above together with an edible carrier or a pharmaceutical matrix. The invention also relates to a probiotic composition comprising a culture supernatant of said strain and/or a metabolite of said strains as defined above together with an edible carrier or a pharmaceutical matrix. More specifically said butyric acid producing strains in this probiotic composition are chosen from *Butyricicoccus pullicaecorum* and strains showing at least 93%, 94%, 95%, 96%, 97%, 98%, 99% or 100% homology to the 16S rRNA sequence of *Butyricicoccus pullicaecorum* characterized by SEQ ID No 1.

According to the present invention, the butyric acid producing strains to be used are incorporated in a carrier which may be a food or a pharmaceutical product, such as e.g. milk, yoghurt, curd, cheese, fermented milks, milk based fermented products, ice-creams, fermented cereal based products, milk based powders, or infant formulae. The carrier may be in the form of tablets, liquid bacterial suspensions, dried oral supplements, wet oral supplement, dry tube feeding or wet tube feeding etc. The carrier may well include other compounds known to be beneficial to an impaired situation of the gastrointestinal tract, e.g., antioxidants, such as Vitamin C, Vitamin E, Selenium or Zinc. Depending on the respective preventive therapy the person skilled in the art will choose the appropriate galenic form and/or supplements, thus assisting in improving the individual's health.

In yet another embodiment the probiotic composition of the present invention further comprises at least one lactic acid bacterium preferably selected among *Lactobacillus casei, Lactobacillus helveticus, Lactobacillus delbrueckii* subspecies *bulgaricus, Lactobacillus paracasei, Lactobacillus acidophilus, Lactococcus lactis, Streptococcus thermophilus, Bifidobacterium longum* and/or *Bifidobacterium breve*.

As referred herein, the lactic acid bacteria comprise generally Gram-positive, low-GC, acid-tolerant, generally non-sporulating, substantially anaerobic rod or cocci that are associated by their common metabolic and physiological characteristics. These bacteria produce lactic acid as the major metabolic end-product of carbohydrate fermentation. The genera that comprise the lactic acid bacteria are preferably chosen from *Lactobacillus, Leuconostoc, Pediococcus, Lactococcus, Streptococcus, Aerococcus, Carnobacterium, Enterococcus, Oenococcus, Sporolactobacillus, Terageno-coccus, Vagococcus, Weisella* and *Lactobacillales*.

In yet another embodiment the composition of the present invention additionally comprises saccharides, preferably oligo- and/or polysaccharides and more preferably inulin and/or fructooligosaccharides.

The addition of saccharide substrates and/or lactic acid bacteria to the composition overcomes problems associated with a low butyrate production when the butyric acid producing strains colonize the gastrointestinal tract. The addition of saccharide substrates such as inulin and/or fructooligosaccharides and/or the addition of other lactic acid bacteria provides substrates for the butyric acid producing strains of the invention.

In another preferred embodiment the present invention relates to a composition and preferably a probiotic composition of the present invention for use in the prophylaxis and/or treatment of intestinal health problems of humans and/or animals.

The butyric acid producing strains to be used according to the present invention may be prepared by a method comprising the steps of:
 introducing a nutrient solution in an incubator vessel,
 making anaerobic conditions,
 autoclaving said vessel,
 introducing an electron acceptor,
 introducing a bacterial culture of a butyrate producing strain as defined above,
 maintaining conditions suitable to allow grow and proliferation of the bacteria; and
 cooling said vessel and contents to a temperature which prevents further growth of bacteria and is suitable for storage of the culture.

The above aspects and embodiments are further supported by the following non-limiting examples.

The present examples demonstrate how the butyric acid producing strains are isolated and on how these strains can be used in the prophylaxis and/or treatment of intestinal health problems.

EXAMPLES

Example 1

Isolation of *Butyricicoccus pullicaecorum*

Using the following strategy *Butyricicoccus pullicaecorum* strains were isolated:
 The strains were isolated from the caecal content of a four week old broiler chicken. The chicken was euthanized and a sample of caecal content was homogenised in anaerobic M2GSC medium as described by Barcenilla et al. (2000). Ten-fold serial dilutions of this suspension were made and from each dilution 0.3 ml was spread onto agar plates containing M2GSC medium with 1.5% agar. Plates were incubated at 42° C., which resembles the body temperature of poultry, for 48 h and single colonies were transferred to tubes with 10 ml of M2GSC broth. All manipulations were performed in an anaerobic workstation (Ruskinn Technology, South Wales, UK). The short-chain fatty acid concentrations in the overnight cultures were analysed using gas liquid chromatography (GC14, Shimadzu, 's Hertogenbosch, The Netherlands). Several butyrate-producing cultures were obtained. The supernatant of these bacterial cultures contained substantial amounts of butyric acid.

So far repetitive element primed (Rep)-PCR using the (GTG) 5 primer and randomly amplified polymorphic DNA (RAPD) typing using the primer 5'-AGCGGGCCAA-3' (SEQ ID NO:2) has been performed as described previously after DNA extraction through an alkaline lysis procedure. The isolates yielded identical or virtually identical DNA fingerprints in both assays, suggesting that the isolates originate from a single strain that colonised the intestinal tract of the sampled chicken.

In order to elucidate the phylogenetic position of the isolates, near-entire 16S rRNA sequences (corresponding to positions 8-1541 in the *Escherichia coli* numbering system) were determined for each isolate using the 'universal' eubacterial primers fD1 and rD1 (Weisburg et al., 1991). The 16S rRNA sequence is provided in table 1. The purified amplicons were sequenced with primers pD, Gamma*, 3 and O* on an ABI PRISM 310 Genetic Analyzer. The closest match to the deduced sequences was found using the FASTA program. The nucleotide sequences were aligned with reference 16S rRNA sequences using the CLUSTAL_W program and a phylogenetic tree was constructed using the neighbour-joining method via the PHYLIP package using DNADIST for distance analysis.

Table 3 enlists the fermentation products produced by the different strains, isolated from the caecal contents of a broiler chicken, grown overnight in M2GSC broth at 42° C. (concentrations (mM) are means of three repeats±standard deviation).

TABLE 3

| Isolate | Acetate | Propionate | Butyrate |
|---|---|---|---|
| 11-3 | −10.6 ± 4.3 | −0.6 ± 1.1 | 13.2 ± 1.0 |
| 25-3 | −14.3 ± 1.7 | −1.4 ± 1.2 | 18.6 ± 1.2 |
| 44-3 | −14.6 ± 3.5 | −1.1 ± 0.3 | 15.5 ± 4.3 |
| 49-3 | −12.4 ± 0.70 | −0.7 ± 0.4 | 18.6 ± 5.1 |
| 54-3 | −11.8 ± 5.9 | −0.2 ± 0.9 | 13.6 ± 0.2 |

Among their closest relatives are members of the *Eubacterium desmolans*. All isolates share virtually identical (98-99%) 16S rRNA sequences. The 16S rRNA sequence is provided in table 1.

Example 2

Effect of Butyric Acid Producing Strains on Colitis

The present example demonstrates the beneficial effects of compositions containing butyrate producing strains such as *Butyricicoccus pullicaecorum* strains.

All strains were cultured in M2GSC-medium pH6 at 41° C. in anaerobic conditions. The 17 h old cultures were centrifuged at 4000 rpm, 15 min at 41° C. The pellet was resuspended in HBSS pH6 supplemented with 1 mg/ml L-cysteine hydrochloride. The number of cfu/ml of both cultures was determined by plating ten-fold dilutions of the bacterial suspension on M2GSC-medium.

The two first two bacterial isolates that were investigated were: *Butyricicoccus pullicaecorum* of the present invention and *Anaerostipes butyraticus*, belonging to clostridial cluster IV and XIVa respectively. *Anaerostipes butyricus* strain which has been deposited at the public BCCM/LMG bacterial collection as *A. butyricus* LMG24724 on Sep. 3, 2008. These two strains together with *Faecalibacterium prausnitzii* and *Anaerostipes caccae*, isolated from human faeces and belonging to clostridium cluster IV and XIVa, were tested for their capacity to decrease inflammation and ulceration in a TNBS-induced colitis model in rats. Colitis was induced on day 7 by intrarectal administration of 10 mg TNBS in 400 µl 50% ethanol. Rats from group 1 to 4 (n=10) received daily (day 1 till day 8), by intragastric gavage, $10^9$ cfu of *F. prausnitzii, B. pullicaecorum, A. caccae* and *A. butyraticus*, respectively. Group 5 was the negative control group, while group 6 was the non-inoculated TNBS-treated positive control group. Forty-eight hours after TNBS instillation, the rats were necropsied. The colon was removed, cut longitudinally and carefully rinsed to remove faecal residues. The weight and the length of the colon were determined as well as the extent of the lesion. These data were used to calculate the colon index (ratio of colon weight vs body weight, mg/g), the colon weight (ratio of colon weight vs colon length, mg/cm) and the ulceration (ratio of extent of damage vs colon length, %), parameters which reflect the severity of the colonic inflammation. Parameters were analyzed using the GLM procedure (Statistical Analysis Systems Institute, 1990) considering a complete randomized design with the inoculated strain as main explanatory variable. Means were compared using a Fisher's protected t-test, and differences were considered significant at P<0.05 (table 4: Parameters reflecting the severity of the colon inflammation expressed by the means. Means within rows with no common superscript differ significantly (P<0.05)). The lesions were scored macroscopically and microscopically. Samples of the inflamed tissue were taken for quantification of TNFα and IL-12 levels. The secretion of TNFα and IL-12 was significantly lower in the group receiving the *B. pullicaecorum* strain compared to the colitis control group. Also from the table it is clear that all parameters were significantly different in the group receiving the *B. pullicaecorum* compared to the positive control group.

Therefore it is clear that the butyrate-producing strains related to *B. pullicaecorum* of the present invention have a beneficial effect on mucosal inflammation seen in ulcerative colitis. This butyrate-producing bacterium should be considered as the next generation probiotic with a mode of action which is related to the production of butyric acid.

TABLE 4

| Parameter | *A. butyraticus* | *B. pullicaecorum* | *A. caccae* | *F. prausnitzii* | Negative | Positive |
|---|---|---|---|---|---|---|
| Colon index (mg/g) | $8.33^a$ | $6.25^b$ | $7.94^a$ | $8.03^a$ | $5.37^b$ | $8.73^a$ |
| Colon weight (mg/cm) | $161.5^a$ | $128.6^b$ | $163.0^a$ | $174.7^a$ | $103.7^b$ | $173.1^a$ |
| Ulceration (%) | $12.3^a$ | $3.19^b$ | $9.85^a$ | $11.2^a$ | $0.00^b$ | $15.2^a$ |
| Macroscopical score | $4.80^{ab}$ | $1.80^c$ | $4.40^b$ | $4.70^{ab}$ | $0.00^c$ | $6.40^a$ |
| Histological score | $14.1^{ab}$ | $8.20^c$ | $13.3^{ab}$ | $12.0^b$ | $0.80^d$ | $15.2^a$ |

Example 3

Effect of Butyric Acid Producing Strains on DSS-Induced Colitis

Thirty-five 4-week old male Wistar rats are obtained from CER Janvier (France) and acclimatized to the study conditions for a period of 14 days. The animals are randomly divided into 4 experimental groups and kept up to five rats per cage. They all have free access to rat pellet feed and water ad libitum. In group 1 and 2, the rats are given daily for 14 days by intragastric gavage, 0.5 ml with 108-109 cfu/ml of *Faecalibacterium prausnitzii* or *Butyricicoccus pullicaecorum*. These strains are cultured in M2GSC-medium pH6.8 at 38° C. in anaerobic conditions. The 20 h old cultures are centrifuged at 4000 rpm, 15 min at 38° C. The pellet is resuspended in HBSS pH 6.8 supplemented with 1 mg/ml L-cysteine hydrochloride. The number of cfu/ml of both cultures is determined by plating ten-fold dilutions of the bacterial suspension on M2GSC-medium. Group 3 and 4 are the control groups and receive daily HBSS pH 6.8 supplemented with 1 mg/ml L-cysteine hydrochloride One week after starting the experiment, the normal drinking water is replaced with water containing 4% DSS. Group 4, the noncolitic group receive water without DSS.

Animal body weight, the presence of gross blood in the faeces and stool consistency are recorded daily. These parameters are used to calculate an average daily disease activity index (DAI) for each animal. All rats are sacrificed on day 7 after starting DSS treatment. The colon is taken from the anus to the cecocolonic junction, cut longitudinally and slightly cleaned with water to remove faecal residues. Afterwards the colon is weighed and its length is measured. Samples of the colon are taken for myeloperoxidase quantification and histological staining. The luminal content and the mucosal scrapings are frozen in −20° C. for analysis of the microbiota.

The results of this experiment demonstrate that the butyrate-producing strains related to *B. pullicaecorum* of the present invention have a beneficial effect on mucosal inflammation.

The invention claimed is:

1. A method of prophylaxis and/or treatment of an intestinal health problem of a human or animal, the method comprising:
   administering to the human or animal a butyric acid producing strain selected from the group consisting of *Butyricicoccus pullicaecorum* deposited at the public BCCM/LMG bacterial collection as *B. pullicaecorum* LMG24109 and strains showing at least 97% homology to the 16S rRNA sequence of *Butyricicoccus pullicaecorum* characterized by SEQ ID No 1.

2. The method according to claim 1, wherein the intestinal health problem of a human or animal is an inflammatory bowel disease, ulcerative colitis, and/or Crohn's disease.

3. The method according to claim 1, wherein the intestinal health problem is associated with colonization of the gastrointestinal tract by a pathogenic microorganism.

4. The method according to claim 1, wherein the intestinal health problem is dysbacteriosis.

5. The method according to claim 1, wherein the butyric acid producing strain is present in a composition comprising an effective amount of the butyric acid producing strain that is sufficiently large to be effectively used in the prophylaxis and/or treatment of an intestinal health problem in a human or animal.

6. The method according to claim 1, wherein administering to the human or animal a butyric acid producing strain comprises administering an amount of the butyric acid producing strain sufficient to colonize the gastrointestinal tract of the human or animal.

7. The method according to claim 1, wherein administering to the human or animal a butyric acid producing strain comprises administering a probiotic composition.

* * * * *

UNITED STATES PATENT AND TRADEMARK OFFICE
CERTIFICATE OF CORRECTION

PATENT NO.        : 8,697,052 B2                                                                Page 1 of 1
APPLICATION NO.   : 13/138461
DATED             : April 15, 2014
INVENTOR(S)       : Van Immerseel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 226 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 2

<210> SEQ ID NO 1
<211> LENGTH: 1482
<212> TYPE: DNA
<213> ORGANISM: Butyricicoccus pullicaecorum

<400> SEQUENCE: 1

```
tagtttgatc ctggctcagg atgaacgctg gcggcgtgcc taacacatgc aagtcgaacg      60
gagttgtttg aggaaatcct tcgggatgga atcttccaac ttagtggcgg acgggtgagt     120
aacgcgtgag caatctgcct ttcagagggg gataacagcc ggaaacggct gctaataccg     180
cataatgcat tgaattcgca tgttttgat gccaaagatt ttatcgctga agatgagct      240 cgcgtctgat tagctagttg gcggggtaac ggcccaccaa ggcgacgatc agtagccgga     300
ctgagaggtt gaacggccac attgggactg aggacacggc ccagactcct accgggaggc     360
agcagtgggg aatattgcgc aatggggggca accctgacgc agcaacgccg cgtgattgat     420
gaaggtcttc ggattgtaaa atctttaat cagggacgaa acaaatgacg gtacctgaag     480
aataagctcc ggctaactac gtgccagcag ccgcggtaat acgtagggag caagcgttat     540
ccggatttac tgggtgtaaa gggcgtgtag gcgggcttgt aagttggaag tgaaatctcg     600
gggcttaacc ccgaaactgc tttcaaaact gcgagtcttg agtgatggag aggcaggcgg     660
aattcccagt gtagcggtga aatgcgtaga tattgggagg aacaccagtg gcgaaggcgg     720
cctgctggac attaactgac gctgaggcgc gaaagcgtgg ggagcaaaca ggattagata     780
ccctggtagt ccacgccgta aacgatggat actaggtgtg ggaggtattg accccttccg     840
tgccggagtt aacacaataa gtatcccacc tggggagtac ggccgcaagg ttgaaactca     900
aaggaattga cggggggcccg cacaagcagt ggagtatgtg gtttaattcg aagcaacgcg     960
caagaacctt accaagtctt gacatcccga tgaccgctcy agagataggg cttttcttcg    1020
gaacatcggt gacaggtggt gcatggttgt cgtcagctcg tgtcgtgaga tgttgggtta    1080
agtcccgcaa cgagcgcaac ccttacgggt tagttgctac gcaagagcac tctagccgga    1140
ctgccgttga caaaacggag gaaggtgggg acgacgtcaa atcatcatgc cccttatgac    1200
ttgggctaca cacgtactac aatggcagtc atacagaggg aagcaaaacc gcgaggtgga    1260
gcaaatccct aaaagctgtc ccagttcaga ttgcaggctg caactcgcct gcatgaagtc    1320
ggaattgcta gtaatcgcgg atcagcatgc cgcggtgaat acgttcccgg gccttgtaca    1380
caccgcccgt cacaccatga gagccggtaa tacccgaagt ccgtagtcta accgcaagga    1440
ggacgcggcc gaaggtagga ctggtaattg ggacgaagtc gt                       1482
```

<210> SEQ ID NO 2
<211> LENGTH: 10
<212> TYPE: DNA
<213> ORGANISM: Butyricicoccus pullicaecorum

<400> SEQUENCE: 2

```
agcgggccaa                                                             10
```